United States Patent [19]

Salowe

[11] Patent Number: 5,776,696
[45] Date of Patent: Jul. 7, 1998

[54] HIGH THROUGHPUT ASSAY USING FUSION PROTEINS

[75] Inventor: Scott P. Salowe, Dayton, N.J.

[73] Assignee: Merck & Co., Inc., Rahway, N.J.

[21] Appl. No.: 707,793

[22] Filed: Sep. 4, 1996

[51] Int. Cl.$^6$ .............. G01N 33/53; G01N 33/546; G01N 33/566; G01N 33/60; G01N 33/68

[52] U.S. Cl. .............. 435/7.1; 435/7.5; 435/7.72; 435/7.8; 530/324; 530/344; 530/350; 536/23.4

[58] Field of Search .............. 435/7.1, 7.5, 7.72, 435/7.8, 969, 973; 530/324, 344, 350, 872, 876, 827; 536/23.4; 930/280

[56] References Cited

U.S. PATENT DOCUMENTS

| | | | |
|---|---|---|---|
| 5,352,660 | 10/1994 | Pawson | 514/12 |
| 5,498,597 | 3/1996 | Burakoff et al. | 514/2 |
| 5,580,979 | 12/1996 | Bachovchin | 540/509 |

OTHER PUBLICATIONS

Edalji et al. High–level expression of recombinant human FK–binding protein from a fusion precursor. Journal of Protein Chemistry. vol. 11, No. 3, pp. 213–223, 1992.

Gilmer et al. Peptide inhibitors of src SH3–SH2–phosphoprotein interactions. The Journal of Biological Chemistry. vol. 269, No. 50, pp. 31711–31719, Dec. 16, 1994.

Jin et al. The 25–kDa FK506–binding protein is localized in the nucleus and associates with casein kinase II and nucleolin. Proceedings of the National Academy of Sciences, USA. vol. 90, pp. 7769–7773, Aug. 1993.

Müller et al. Rapid identification of phosphopeptide ligands for SH2 domains: screening of peptide libraries by fluorescence–activated bead sorting. The Journal of Biological Chemistry. vol. 271, No. 28, pp. 16500–16505, Jul. 12, 1996.

Sampson et al. Neisseria meningitidis encodes an FK506–inhibitable rotamase. Proceedings of the National Academy of Sciences, USA. vol. 89, pp. 1164–1168, Feb. 1992.

Lerner, et al., "Scintillation Proximity Assay for Human DNA Topoisomerase I Using Recombinant Biotinyl–Fusion Protein Produced in Baculovirus–Infected Insect Cells", Anal. Biochem., vol. 240, pp. 289–297 (1996).

Skinner, et al., "Direct Measurment of the Binding of RAS to Neurofibromin Using a Scintillation Proximity Assay", Anal. Biochem., vol. 233, pp. 259–265, (1994).

Lemmon, et al., "Thermodynamic Studies of Tyrosyl–Phosphopeptide Binding to the SH2 Domain of p56lck", Biochemistry, vol. 33, pp. 5070–5076, 1994.

Payne, et al., "Kinetics of p56lck and p60src Homology 2 Domain Binding to Tyrosine–Phosphorylated Peptides Determined by a Competition Assay or Surface Plasmon Resonance", Proc. Natl. Acad. Sci. USA, vol. 90, pp. 4902–4906, 1993.

Isakov, et al., ZAP–70 Binding Specificity to T Cell Receptor Tyrosine–Based Activation Motifs: The Tandem SH2 Domains of ZAP–70 Bind District Tyrosine–Based Activation Motifs with Varying Affinity, J. Exp. Med., vol. 181, pp. 375–380, 1995.

Huyer, et al., "Direct Determination of the Sequence Recognition Requirements of the SH2 Domains of SH–PTP2", Biochemistry, vol. 34, pp. 1040–1049, 1995.

(List continued on next page.)

Primary Examiner—Elizabeth C. Kemmerer
Assistant Examiner—Brian Lathrop
Attorney, Agent, or Firm—Valerie J. Camara; Mark R. Daniel; Dianne Pecoraro

[57] ABSTRACT

This application describes a high throughput assay for screening for compounds which are capable of binding to a fusion protein which consists of a target protein and an FKS506-binding protein.

10 Claims, 1 Drawing Sheet

OTHER PUBLICATIONS

Panayotou, et al., "Interactions Between SH2 Domains and Tyrosine–Phosphorylated Platelet–Derived Growth Factor Beta–Receptor Sequences: Analysis of Kinetic Parameters by a Novel Biosenor–Based Approach", Mol. Cell. Biol., vol. 13, pp. 3567–3576, 1993.

Felder, et al., "SH2 Domains Exhibit High–Affinity Binding to Tyrosine–Phosphorylated Peptides Yet Also Exhibit Rapid Dissociation and Exchange", Mol. Cell. Biol., vol. 13, pp. 1449–1455, 1993.

Morelock, et al., "Determination of Receptor–Ligand Kinetic and Equilibrium Binding Constants Using Surface Plasmon Resonance: Application to the lck SH2 Domain and Phosphotyrosyl Peptides", J. Med. Chem., vol. 38, pp. 1309–1318, 1995.

Ladbury, et al., "Measurement of the Binding of Tyrosyl Phosphopeptides to SH2 Domains: A Reappraisal", Proc. Natl. Acad. Sci. USA, vol. 92, pp. 3199–323, 1995.

Piccione, et al., "Phosphatidylinositol 3–Kinase p85 SH2 Domain Specificity Defined by Direct Phosphopeptide/SH2 Domain Binding", Biochemistry, vol. 32(13), pp. 3197–3202, 1993.

Sonatore, et al., "The Utility of FK506–Binding Protein as a Fusion Partner in Scintillation Proximity Assays: Appliction to SH2 Domains", Anal. Biochemistry, vol. 240, pp. 289–297, 1996.

Signal detected

FIG. 1A

Signal not detected

FIG. 1B

HIGH THROUGHPUT ASSAY USING FUSION PROTEINS

DOMESTIC PRIORITY CLAIM

The priority of U.S. Provisional application Ser. No. 60/003,824, filed on Sep. 15, 1995, now abandoned, is claimed.

BACKGROUND OF THE INVENTION

Src homology 2 (SH2) domains are a family of homologous protein domains that share the common property of recognizing phosphorylated tyrosine residues in specific peptide contexts. They have routinely been expressed in *E. coli* as fusion proteins with glutathione-S-transferase (GST). This usually provides high level expression and straightforward affinity purification on glutathione-Sepharose. Ligand binding is then assayed by incubating the GST/SH2 with a radiolabeled phosphopeptide, precipitating the complex with glutathione-Sepharose, washing the beads, and then counting the beads to determine bound radioactivity [Isakov et al., *J. Exp. Med.*, 181, 375-380 (1995); Piccione et al., *Biochemistry*, 32, 3197-3202 (1993); Huyer et al., *Biochemistry*, 34, 1040-1049 (1995)]. There are several disadvantages to this procedure, particularly when applied to high-throughput screening for agonists, antagonists, or inhibitors as new leads for drug development. First, the radiolabeling of the peptide is carried out either enzymatically with a kinase and [$^{32}$P]ATP or chemically with [$^{125}$I] Bolton-Hunter reagent. In both cases, the isotopes are short-lived and thus require frequent preparation of material. In the case of enzymatic phosphorylation, the appropriate kinase must also be available in sufficient quantity to generate enough material for screening purposes. Second, the protocol requires separation of bound complex from free phosphopeptide by washing of the glutathione-Sepharose beads. This is a nonequilibrium procedure that risks dissociation of the bound ligand, particularly when off-rates are fast. Thus, there is the possibility of misleading results. Finally, due to the number of manipulations and centrifugations involved, the protocol is very tedious to conduct manually and is not readily adaptable to robotic automation to increase throughput.

Two additional methods for measuring the interaction of proteins and ligands that have been applied to SH2 domains are biospecific interaction analysis using surface plasmon resonance and isothermal titration calorimetry (Felder et al., *Mol. Cell. Biol.*, 13, 1449-1455 (1993); Panayotou et al., *Mol. Cell. Biol.*, 13, 3567-3576 (1993); Payne et al., *Proc. Natl. Acad. Sci. U.S.A.*, 90, 4902-4906 (1993); Morelock et al., *J. Med. Chem.* 38, 1309-18 (1995); Ladbury et al., *Proc. Natl. Acad. Sci. U.S.A.*, 92, 3199-3203 (1995); Lemmon et al., *Biochemistry*, 33, 5070-5076 (1994)). These techniques do not require a particular fusion partner for the SH2 domain, but do require sophisticated instrumentation that is not amenable to high throughput screening.

SUMMARY OF THE INVENTION

The instant invention covers a method of screening for compounds capable of binding to a fusion protein which comprises combining a test compound, a tagged ligand, a fusion protein (target protein, peptide linker and FK506-binding protein), a radiolabeled ligand, and coated scintillation proximity assay (SPA) beads, and then measuring the scintillation counts attributable to the binding of the tagged ligand to the fusion protein in the presence of the test compound relative to a control assay in the absence of the test compound, so as to determine the effect the test compound has on the binding of the tagged ligand. This invention provides an immediate means of making use of SPA technology for the functional assay of ligand binding to a single or multiple signal transduction domain(s), for example a phosphopeptide binding to an SH2 domain. The present invention does not require specialized radiochemical synthesis and is readily adaptable to robotic automation for high capacity screening for agonists, antagonists, and/or inhibitors.

BRIEF DESCRIPTION OF THE FIGURES

FIG. 1.

A.) Binding of the streptavidin SPA bead, biotinylated ligand and the fusion protein (SH2:FKBP), which emits a detectable signal; and B.) Binding of the test compound and the fusion protein (SH2:FKBP), which results in no signal detection.

DETAILED DESCRIPTION OF THE INVENTION

The present invention relates to a method of screening for compounds which preferentially bind to a target protein.

An embodiment of this invention is a method of screening for compounds capable of binding to a fusion protein which comprises the steps of:

a) mixing a test compound, a tagged ligand, the fusion protein, a radiolabeled ligand and coated scintillation proximity assay (SPA) beads;

b) incubating the mixture for between about 1 hour and about 24 hours;

c) measuring the SPA bead-bound counts attributable to the binding of the tagged ligand to the fusion protein in the presence of the test compound using scintillation counting; and d) determining the binding of the tagged ligand to the fusion protein in the presence of the test compound relative to a control assay run in the absence of the test compound.

The term "fusion protein" refers to a "target protein" fused to an "FK506-binding protein" (FKBP), the two proteins being separated by a "peptide linker".

A "peptide linker" may consist of a sequence containing from about 1 to about 20 amino acids, which may or may not include the sequence for a protease cleavage site. An example of a peptide linker which is a protease cleavage site is represented by the amino acid sequence GLUPRGS (SEQ.ID.NO: 7).

The term "target protein" refers to any protein that has a defined ligand. Included within this definition of target protein are single and multiple signal transduction domains, such as, but not limited to, Src homology 1 (SH1), Src homology 2 (SH2), Src homology 3 (SH3), and pleckstrin homology (PH) domains [Hanks & Hunter, *FASEB J.*, 9, 576-596 (1995); Bolen, *Curr. Opin. Immunol.*, 7, 306-311 (1995); Kuriyan & Cowburn, *Curr. Opin. Struct. Biol.*, 3, 828-837 (1993); Cohen et al., *Cell*, 80, 237-248 (1995)]. The term "SH1 domain" refers to a family of homologous protein domains that bind ATP and catalyze tyrosine phosphorylation of peptide and protein substrates. The term "SH2 domain" refers to a family of homologous protein domains that share the common property of recognizing phosphorylated tyrosine residues in specific peptide contexts. The term "SH3 domain" refers to a family of homologous protein domains that share the common property of recognizing polyproline type II helices. The term "PH domain" refers to a family of homologous protein domains that mediate both protein-protein and protein-lipid interactions. Examples of SH2 domains which may be utilized in the method of the invention include, but are not limited to, the single and tandem SH2 domains present in the tyrosine kinases ZAP, SYK and LCK. The DNA sequences were obtained from GenBank. National Center for Biotechnology Information, National Library of Medicine, 8600 Rockville Pike, Bethesda, Md. 20894. The Accession Numbers for the sequences are: human ZAP (LO5148); human SYK (L28824) and human LCK (X13529). The sequences for ZAP, Syk and Lck are disclosed in the sequence listing as follows: the isolated DNA encoding for a fusion protein containing ZAP is (SEQ.ID.NO. 1); the isolated DNA encoding for a fusion protein containing Syk is (SEQ.ID.NO. 2); the isolated DNA encoding for a fusion protein containing Lck is (SEQ.ID.NO. 3); the sequence for the FKBP-ZAP:SH2 fusion protein is (SEQ.ID.NO. 4); the sequence for the FKBP-Syk:SH2 fusion protein is (SEQ.ID.NO. 5); and the sequence for the FKBP-Lck:SH2 fusion protein is (SEQ.ID.NO. 6).

The term "tagged ligand" refers to a biotinylated or epitope tagged ligand for the target protein.

The term "radiolabeled ligand" refers to a [$^3$H]- or [$^{125}$I] -labeled ligand which binds to the FKBP. An example of a radiolabeled ligand useful in the instant invention is [$^3$H]-dihydroFK506.

The term "coated scintillation proximity assay beads" (SPA beads) refers to streptavidin-coated scintillation proximity assay beads when the tagged ligand is biotinylated, and to anti-epitope antibody bound to anti-antibody-coated or protein A-coated scintillation proximity assay beads when the tagged ligand is epitope-tagged.

The term "control assay" refers to the assay when performed in the presence of the tagged ligand, the fusion protein, the radiolabeled ligand and the coated scintillation proximity assay beads, but in the absence of the test compound.

The term FK506-binding proteins may include, but are not limited to, the below listed FKBPs and FKBP homologues, which include a citation to the references which disclose them. This list is not intended to limit the scope of the invention.

| Mammalian | |
|---|---|
| FKBP-12 | Galat et al., Eur. J. Biochem., 216:689–707 (1993). |
| FKBP-12.6 | Wiederrecht, G. and F. Etzkorn Perspectives in Drug Discovery and Design, 2:57–84 (1994). |
| FKBP-13 | Galat et al., supra; Wiederrecht and Etzkorn, supra. |
| FKBP-25 | Galat et al., supra; Wiederrecht and Etzkorn, supra. |
| FKBP-38 | Wiederrecht and Etzkorn, supra. |
| FKBP-51 | Baughman et al., Mol. Cell. Biol., 8, 4395–4402 (1995). |
| FKBP-52 | Galat et al., supra. |
| Bacteria | |
| Legionella pnemnophilia | Galat et al., supra. |
| Legionella micadei | Galat et al., supra. |
| Chlamydia trachomatis | Galat et al., supra. |
| E. coli fkpa | Home, S. M. and K. D. Young, Arch. Microbiol., 163:357–365 (1995). |
| E. coli slyD | Roof et al., J. Biol. Chem. 269:2902–2910 (1994). |
| E. coli orf149 | Trandinh et al., FASEB J. 6:3410–3420 (1992). |
| Neisseria meningitidis | Hacker, J. and G. Fischer, Mol. Micro., 10:445–456 (1993). |
| Streptomyces chrysomallus | Hacker and Fischer, supra. |
| Fungal | |
| yeast FKBP-12 | Cardenas et al., Perspectives in Drug Discovery and Design, 2:103–126 (1994). |
| yeast FKBP-13 | Cardenas et al., supra. |
| yeast NPR1(FPR3) | Cardenas et al., supra. |
| Neurospora | Galat et al., supra. |

A variety of host cells may be used in this invention, which include, but are not limited to, bacteria, yeast, bluegreen algae, plant cells, insect cells and animal cells.

Expression vectors are defined herein as DNA sequences that are required for the transcription of cloned copies of genes and the translation of their mRNAs in an appropriate host. Such vectors can be used to express genes in a variety of host cells, such as, bacteria, yeast, bluegreen algae, plant cells, insect cells and animal cells.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available vectors suitable for FKBP fusion protein expression include, but are not limited to pBR322 (Promega), pGEX (Amersham), pT7 (USB), pET (Novagen), pIBI (IBI), pProEX-1 (Gibco/BRL), pBluescript II (Stratagene), pTZ18R and pTZ19R (USB), pSE420 (Invitrogen), pVL1392 (Invitrogen), pBlueBac (Invitrogen), pBAcPAK (Clontech), pHIL (Invitrogen), pYES2 (Invitrogen), pCDNA (Invitrogen), pREP (Invitrogen) or the like.

The expression vector may be introduced into host cells via any one of a number of techinques including but not limited to transformation, transfection, infection, protoplast fusion, and electroporation.

E. coli containing an expression plasmid with the target gene fused to FKBP are grown and appropriately induced. The cells are then pelleted and resuspended in a suitable buffer. Although FKBP-12 lacks sequences that specifically direct it to the periplasm, FKBP fusions are primarily located there and can be released by a standard freeze/thaw treatment of the cell pellet. Following centrifugation, the resulting supernatant contains >80% pure FKBP fusion, which if desired can be purified further by conventional methods. Alternatively, the assay is not dependent on pure protein and the initial periplasmic preparation may be used directly. A thrombin site located between FKBP and the target protein can be used as a means to cleave FKBP from the fusion; such cleaved material may be a suitable negative control for subsequent assays.

A fusion protein which contains a single or multiple SH2 domain(s) may be purified by preparing an affinity matrix consisting of biotinylated phosphopeptide coupled to avidin or streptavidin immobilized on a solid support. A freeze/thaw extract is prepared from the cells which express the fusion protein and is loaded onto the affinity matrix. The desired fusion protein is then specifically eluted with phenyl phosphate.

Figure 1A:
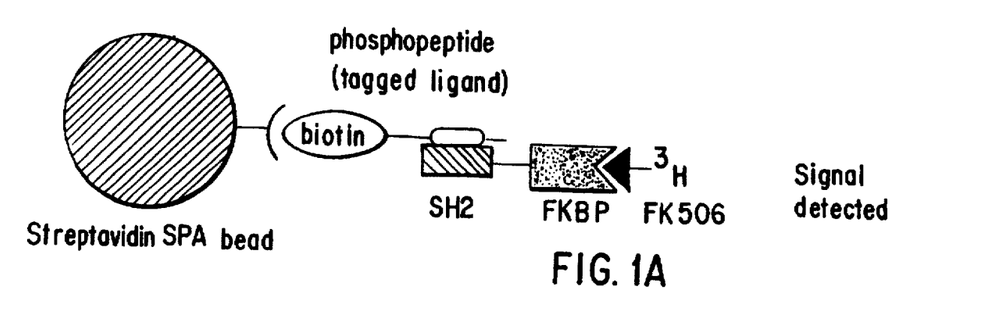
Figure 1B:
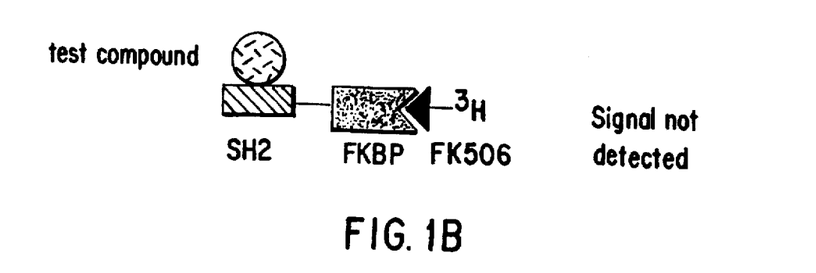

To assay the formation of a complex between a target protein and its ligand, the tagged ligand is mixed with the FKBP fusion protein in a suitable buffer in the presence of the radiolabeled ligand in the well of a white microplate. After a suitable incubation period to allow complex formation to occur, coated SPA beads are added to capture the tagged ligand and any bound fusion protein. The plate is sealed, incubated for a sufficient period to allow the capture to go to completion, then counted in a multiwell scintillation counter. Screening for agonists/antagonists/inhibitors is carried out by performing the initial incubation prior to the capture step with SPA beads in the presence of a test compound(s) to determine whether they have an effect upon the binding of the tagged ligand to the fusion protein. This principle is illustrated by FIG. 1.

The present invention can be understood further by the following examples, which do not constitute a limitation of the invention.

EXAMPLE 1

Process for Preparing the FKBP fusion cloning vector

General techniques for modifying and expressing genes in various host cells can be found in Ausubel, F. M., Brent, R., Kingston, R. E., Moore, D. D., Seidman, J. G., Smith, J. A. and Struhl, K. Current Protocols in Molecular Biology (John Wiley & Sons, New York, N.Y., 1989). Sequences for a 3'-altered FKBP fragment that contained a glycine codon (GGT) in place of the stop (TGA) codon followed by a sequence encoding a thrombin site (Leu-Val-Pro-Arg) and BamHI restriction site (GAATTC) were amplified using the polymerase chain reaction (PCR). The PCR reaction contained the following primers: 5'-GATCGCCATGGGAGTGCAGGTGGAAACCATCT-CCCCA-3' (SEQ.ID.NO. 8) and 5'-TACGAATTCTGGCGTGGATCCACGCGGAACCAG-ACCTTCCAGT TTTAG-3' (SEQ.ID.NO. 9) and a plasmid containing human FKBP-12 as the template. The resulting 367 base pair amplification product was ligated into the vector pCRII (Invitrogen) and the ligation mixture transformed into competent *Escherichia coli* cells. Clones containing an insert were identified using PCR with flanking vector primers. Dideoxy DNA sequencing confirmed the nucleotide sequence of one positive isolate. The altered 338 base pair FKBP fragment was excised from the pCRII plasmid using NcoI and BamHI and ligated into NcoI and BamHI digested pET9d (Novagen) plasmid. Competent *E. coli* were transformed with the ligation mixture, and colonies containing the insert were identified using PCR with primers encoding for flanking vector sequences. The FKBP fusion cloning vector is called pET9dFKBPt.

EXAMPLE 2

Process for Preparing the FK-ZAP fusion expression vector

A DNA fragment encoding for the tandem SH2 domains of ZAP-70 was prepared by PCR to contain a BamHI site at the 5'-end such that the reading frame was conserved with that of FKBP in the fusion vector. At the 3'-end, the fragment also incorporated a stop codon followed by a BamHI site. The PCR reaction contained Molt-4 cDNA (Clontech) and the following primers: 5'-ATTAGGATCCATGCCAGATCCTGCAGCTCACCT-GCCCT-3' (SEQ.ID.NO. 10) and 5'-ATATGGATCCTTACCAGAGGCGTTGCT-3' (SEQ.ID.NO. 11). The fragment was cloned into a suitable vector, sequenced, digested with BamHI, and the insert containing the SH2 domains ligated to BamHI treated pET9dFKBPt, and transformed into *E. coli*. Clones containing inserts in the correct orientation were identified by PCR or restriction enzyme analysis. Plasmid DNA was prepared and used to transform BL21(DE3) cells.

EXAMPLE 3

Process for Preparing the FK-SYK fusion expression vector

The expression vector for the tandem SH2 domains of Syk fused to FKBP was prepared as in Example 2 except that the PCR reaction contained Raji cell cDNA (Clontech) and the following primers: 5'-CAATAGGATCCATGGCCAGCAGCGGCATGGC-TGA-3' (SEQ.ID.NO. 12) and 5'-GACCTA-GGATCCCTAATTAACATTTCCCTGTGTGCCGAT-3' (SEQ.ID.NO. 13).

EXAMPLE 4

Process for Preparing the FK-LCK fusion expression vector

The expression vector for the SH2 domain of Lck fused to FKBP was prepared as in Example 2 except that the PCR reaction contained Molt-4 cDNA (Clontech) and the following primers: 5'-ATATGGATCCATGGCGAA-CAGCCTGGAGCCCGAACCCT-3' (SEQ.ID.NO. 14) and 5'-ATTAGGATCCTTAGGTCTGGCAGGGGCGGCTC-AACCGTGT GCA-3' (SEQ.ID.NO. 15).

EXAMPLE 5

FK-ZAP

Step A: Process for Expression of FK-ZAP

*E. coli* BL21(DE3) cells containing the pET9dFKBPt/ZapSH2 plasmid were grown in Luria-Bertani (LB) media containing 50 microgram/ml kanamycin at 37 degrees C. until the optical density measured at 600 nm was 0.5–1.0. Expression of the FK-ZAP fusion protein was induced with 0.1 mM isopropyl beta-thiogalactopyranoside and the cells were grown for another 3–5 hr at 30 degrees C. They were pelleted at 4400×g for 10 min at 4 degrees C. and resuspended in 2% of the original culture volume with 100 mM tris pH 8.0 containing 1 microgram/ml each aprotinin, pepstatin, leupeptin, and bestatin. The resuspended pellet was frozen at –20 degrees C. until further purification.

Step B: Process for Purification of FK-ZAP

The affinity matrix for purification of FK-ZAP was prepared by combining agarose-immobilized avidin with excess biotinylated phosphopeptide derived from the ζ1 ITAM sequence of the human T-cell receptor, biotinyl-GSNQLpYNELNLGRREEpYDVLDK (SEQ.ID.NO. 16), and washing out unbound peptide. Frozen cells containing FK-ZAP were thawed in warm water, refrozen on dry ice for about 25 min., then thawed again. After the addition of 0.1% octyl glucoside, 1 mM dithiothreitol (DTT) and 500 mM NaCl, the extract was centrifuged at 35.000×g for approximately 30 minutes. The supernatant was loaded onto the phosphopeptide affinity column, at about 4° and washed with phosphate buffered saline containing 1 mM DTT and 0.1% octyl glucoside. FK-ZAP was eluted with 200 mM phenyl phosphate in the same buffer at about 37°. The protein pool was concentrated and the phenyl phosphate removed on a desalting column. The purified FK-ZAP was stored at about –30° in 10 mM HEPES/150 mM NaCl/1 mM DTT/0.1 mM EDTA/10% glycerol.

EXAMPLE 6

FK-SYK

*E. coli* BL21(DE3) cells containing the pET9dFKBPt/SykSH2 plasmid were grown, induced, and harvested as described in Example 5. FK-SYK was purified using the same affinity matrix and methodology described in Example 5.

EXAMPLE 7

FK-LCK

*E. coli* BL21(DE3) cells containing the pET9dFKBPt/LckSH2 plasmid were grown, induced, and harvested as described in Example 5. The affinity matrix for purification of FK-LCK was prepared by combining agarose-immobilized avidin with excess biotinyl-EPQpYEEIPIYL, and washing out unbound peptide. The remaining methodology for purification was the same as Example 5.

EXAMPLE 8

Method of Screening for Antagonists of FK-ZAP

Assays were conducted at ambient temperature in a buffer consisting of 25 mM HEPES, 10 mM DTT, 0.01% TWEEN-20, pH 7.0. 10 µl of a DMSO solution of test compound(s) and 120 µl of biotinyl-phosphopeptide stock solution were dispensed into the wells of a 96-well Packard Optiplate. Next, 20 µl of a mixture of FK-ZAP protein and $^3$H-dihydroFK506 were added to each test well. Finally, 50 µl of a 4 mg/ml suspension of SPA beads were dispensed to each well. Final concentrations of the assay components were:

25 nM biotinyl-GSNQLpYNELNLGRREEpYDVLDK (SEQ.ID.NO. 16)
25 nM FK-ZAP fusion protein
10 nM $^3$H-dihydroFK506 (DuPont NEN)
1.0 mg/ml streptavidin-SPA beads (Amersham)
5% DMSO The plate was sealed and incubated between 1 and 8 hours. Bead-bound radioactivity was then measured in a Packard Topcount microplate scintillation counter.

EXAMPLE 9

Method of Screening for Antagonists of FK-SYK

The assays were conducted as set forth in Example 8, except that FK-SYK replaced FK-ZAP.

EXAMPLE 10

Method of Screening for Antagonists of FK-LCK

The assays were conducted as set forth in Example 8, except that FK-LCK replaced FK-ZAP and the tagged ligand was 25 nM biotinyl-EPQpYEEIPIYL (SEQ.ID.NO. 17).

---

What is claimed is:

1. A method of screening for compounds capable of binding to a fusion protein, which is defined as an FK506-binding protein linked to a target protein through a peptide linker, which comprises the steps of:

a) mixing a test compound, a tagged ligand for the target protein, which is selected from a biotinylated ligand or an epitope-tagged ligand, the fusion protein, a radiolabeled ligand selected from [$^3$H]- or [$^{125}$I]-labeled FK506 analog and coated scintillation proximity assay (SPA) beads selected from streptavidin-coated or anti-antibody coated or protein A-coated beads;

b) incubating the mixture from between about 1 hour to about 24 hours;

c) measuring the SPA bead-bound counts attributable to the binding of the tagged ligand to the fusion protein in the presence of the test compound using scintillation counting; and     d) determining the binding of the tagged ligand to the fusion protein in the presence of the test compound relative to a control assay run in the absence of the test compound.

2. The method of screening for compounds capable of binding to a fusion protein, as recited in claim 1, wherein the target protein comprises a single or multiple signal transduction domain.

3. The method of screening for compounds capable of binding to a fusion protein, as recited in claim 2, wherein the single or multiple signal transduction domain is selected from the group consisting of: SH1, SH2, SH3 and PH domains.

4. The method of screening for compounds capable of binding to a fusion protein, as recited in claim 3, wherein the target protein is a single or multiple SH2 domain.

5. The method of screening for compounds capable of binding to a fusion protein, as recited in claim 4, wherein the radiolabeled ligand is [$^3$H]-dihydroFK506.

6. The method of screening for compounds capable of binding to a fusion protein, as recited in claim 5, wherein the FK506-binding protein is a 12 kDA human FK506-binding protein.

7. The method of screening for compounds capable of binding to a fusion protein, as recited in claim 6, wherein the target protein is a single or multiple SH2 domain selected from the group consisting of: ZAP:SH2, SYK:SH2 and LCK:SH2.

8. The method of screening for compounds capable of binding to a fusion protein, as recited in claim 7, wherein the target protein is the SH2 domain, ZAP:SH2.

9. The method of screening for compounds capable of binding to a fusion protein, as recited in claim 7, wherein the target protein is the SH2 domain, SYK:SH2.

10. The method of screening for compounds capable of binding to a fusion protein, as recited in claim 7, wherein the target protein is the SH2 domain, LCK:SH2.

\* \* \* \* \*

UNITED STATES PATENT AND TRADEMARK OFFICE
CERTIFICATE OF CORRECTION

PATENT NO. : 5,776,696

DATED : 7/7/98

INVENTOR(S) : Scott P. Salowe

It is certified that error appears in the above-identified patent and that said Letters Patent is hereby corrected as shown below:

On the title page, following box [73], insert

-- [*] Notice: The term of this patent shall not extend beyond the expiration date of Patent No. 5,783,398. --

Signed and Sealed this

Twenty-seventh Day of October, 1998

Attest:

BRUCE LEHMAN

*Attesting Officer*       *Commissioner of Patents and Trademarks*

UNITED STATES PATENT AND TRADEMARK OFFICE
CERTIFICATE OF CORRECTION

PATENT NO. : 5,776,696

DATED : 7/7/98

INVENTOR(S) : Scott P. Salowe

It is certified that error appears in the above-identified patent and that said Letters Patent is hereby corrected as shown below:

On the title page, after item [22] insert:

-- Related U.S. Application Data
 [60] Provisional application No. 60/003,824, September 15, 1995.--

Signed and Sealed this

Twenty-third Day of February, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 1137 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:1:

```
ATGGGAGTGC  AGGTGGAAAC  CATCTCCCCA  GGAGATGGAC  GCACCTTCCC  CAAGCGCGGC    60
CAGACCTGCG  TGGTGCACTA  CACCGGGATG  CTTGAAGATG  GAAAGAAATT  TGATTCCTCC   120
CGGGACAGAA  ACAAGCCCTT  TAAGTTTATG  CTAGGCAAGC  AGGAGGTGAT  CCGAGGCTGG   180
GAAGAAGGGG  TTGCCCAGAT  GAGTGTGGGT  CAGAGAGCCA  AACTGACTAT  ATCTCCAGAT   240
TATGCCTATG  GTGCCACTGG  GCACCCAGGC  ATCATCCCAC  CACATGCCAC  TCTCGTCTTC   300
GATGTGGAGC  TTCTAAAACT  GGAAGGTCTG  GTTCCGCGTG  GATCCATGCC  AGATCCTGCA   360
GCTCACCTGC  CCTTCTTCTA  CGGCAGCATC  TCGCGTGCCG  AGGCCGAGGA  GCACCTGAAG   420
CTGGCGGGCA  TGGCGGACGG  GCTCTTCCTG  CTGCGCCAGT  GCCTGCGCTC  GCTGGGCGGC   480
TATGTGCTGT  CGCTCGTGCA  CGATGTGCGC  TTCCACCACT  TTCCCATCGA  GCGCCAGCTC   540
AACGGCACCT  ACGCCATTGC  CGGCGGCAAA  GCGCACTGTG  GACCGGCAGA  GCTCTGCGAG   600
TTCTACTCGC  GCGACCCCGA  CGGGCTGCCC  TGCAACCTGC  GCAAGCCGTG  CAACCGGCCG   660
TCGGGCCTCG  AGCCGCAGCC  GGGGGTCTTC  GACTGCCTGC  GAGACGCCAT  GGTGCGTGAC   720
TACGTGCGCC  AGACGTGGAA  GCTGGAGGGC  GAGGCCCTGG  AGCAGGCCAT  CATCAGCCAG   780
GCCCCGCAGG  TGGAGAAGCT  CATTGCTACG  ACGGCCCACG  AGCGGATGCC  CTGGTACCAC   840
AGCAGCCTGA  CGCGTGAGGA  GGCCGAGCGT  AAACTTTACT  CTGGGGCGCA  GACCGACGGC   900
AAGTTCCTGC  TGAGGCCGCG  GAAGGAGCAG  GGCACATACG  CCCTGTCCCT  CATCTATGGG   960
```

-continued

| AAGACGGTGT | ACCACTACCT | CATCAGCCAA | GACAAGGCGG | GCAAGTACTG | CATTCCCGAG | 1020 |
| GGCACCAAGT | TTGACACGCT | CTGGCAGCTG | GTGGAGTATC | TGAAGCTGAA | GGCGGACGGG | 1080 |
| CTCATCTACT | GCCTGAAGGA | GGCCTGCCCC | AACAGCAGTG | CCAGCAACGC | CTCTTAA | 1137 |

( 2 ) INFORMATION FOR SEQ ID NO:2:

( i ) SEQUENCE CHARACTERISTICS:
        ( A ) LENGTH: 1155 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:2:

| ATGGGAGTGC | AGGTGGAAAC | CATCTCCCCA | GGAGATGGAC | GCACCTTCCC | CAAGCGCGGC | 60 |
| CAGACCTGCG | TGGTGCACTA | CACCGGGATG | CTTGAAGATG | GAAAGAAATT | TGATTCCTCC | 120 |
| CGGGACAGAA | ACAAGCCCTT | TAAGTTTATG | CTAGGCAAGC | AGGAGGTGAT | CCGAGGCTGG | 180 |
| GAAGAAGGGG | TTGCCCAGAT | GAGTGTGGGT | CAGAGAGCCA | AACTGACTAT | ATCTCCAGAT | 240 |
| TATGCCTATG | GTGCCACTGG | GCACCCAGGC | ATCATCCAC | CACATGCCAC | TCTCGTCTTC | 300 |
| GATGTGGAGC | TTCTAAAACT | GGAAGGTCTG | GTTCCGCGTG | GATCCATGGC | CAGCAGCGGC | 360 |
| ATGGCTGACA | GCGCCAACCA | CCTGCCCTTC | TTTTTCGGCA | ACATCACCCG | GGAGGAGGCA | 420 |
| GAAGATTACC | TGGTCCAGGG | GGGCATGAGT | GATGGGCTTT | ATTTGCTGCG | CCAGAGCCGC | 480 |
| AACTACCTGG | GTGGCTTCGC | CCTGTCCGTG | GCCCACGGGA | GGAAGGCACA | CCACTACACC | 540 |
| ATCGAGCGGG | AGCTGAATGG | CACCTACGCC | ATCGCCGGTG | GCAGGACCCA | TGCCAGCCCC | 600 |
| GCCGACCTCT | GCCACTACCA | CTCCCAGGAG | TCTGATGGCC | TGGTCTGCCT | CCTCAAGAAG | 660 |
| CCCTTCAACC | GGCCCCAAGG | GGTGCAGCCC | AAGACTGGGC | CCTTTGAGGA | TTTGAAGGAA | 720 |
| AACCTCATCA | GGGAATATGT | GAAGCAGACA | TGGAACCTGC | AGGGTCAGGC | TCTGGAGCAG | 780 |
| GCCATCATCA | GTCAGAAGCC | TCAGCTGGAG | AAGCTGATCG | CTACCACAGC | CCATGAAAAA | 840 |
| ATGCCTTGGT | TCCATGGAAA | AATCTCTCGG | GAAGAATCTG | AGCAAATTGT | CCTGATAGGA | 900 |
| TCAAAGACAA | ATGGAAAGTT | CCTGATCCGA | GCCAGAGACA | ACAACGGCTC | CTACGCCCTG | 960 |
| TGCCTGCTGC | ACGAAGGGAA | GGTGCTGCAC | TATCGCATCG | ACAAAGACAA | GACAGGGAAG | 1020 |
| CTCTCCATCC | CCGAGGGAAA | GAAGTTCGAC | ACGCTCTGGC | AGCTAGTCGA | GCATTATTCT | 1080 |
| TATAAAGCAG | ATGGTTTGTT | AAGAGTTCTT | ACTGTCCCAT | GTCAAAAAAT | CGGCACACAG | 1140 |
| GGAAATGTTA | ATTAG | | | | | 1155 |

( 2 ) INFORMATION FOR SEQ ID NO:3:

( i ) SEQUENCE CHARACTERISTICS:
        ( A ) LENGTH: 675 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:3:

| ATGGGAGTGC | AGGTGGAAAC | CATCTCCCCA | GGAGATGGAC | GCACCTTCCC | CAAGCGCGGC | 60 |
| CAGACCTGCG | TGGTGCACTA | CACCGGGATG | CTTGAAGATG | GAAAGAAATT | TGATTCCTCC | 120 |
| CGGGACAGAA | ACAAGCCCTT | TAAGTTTATG | CTAGGCAAGC | AGGAGGTGAT | CCGAGGCTGG | 180 |
| GAAGAAGGGG | TTGCCCAGAT | GAGTGTGGGT | CAGAGAGCCA | AACTGACTAT | ATCTCCAGAT | 240 |

-continued

```
TATGCCTATG GTGCCACTGG GCACCCAGGC ATCATCCAC  CACATGCCAC TCTCGTCTTC    300
GATGTGGAGC TTCTAAAACT GGAAGGTCTG GTTCCGCGTG ATCCATGGC  GAACAGCCTG    360
GAGCCCGAAC CCTGGTTCTT CAAGAACCTG AGCCGCAAGG ACGCGGAGCG GCAGCTCCTG    420
GCGCCCGGGA ACACTCACGG CTCCTTCCTC ATCCGGGAGA GCGAGAGCAC CGCGGGATCG    480
TTTTCACTGT CGGTCCGGGA CTTCGACCAG AACCAGGGAG AGGTGGTGAA ACATTACAAG    540
ATCCGTAATC TGGACAACGG TGGCTTCTAC ATCTCCCCTC GAATCACTTT TCCCGGCCTG    600
CATGAACTGG TCCGCCATTA CACCAATGCT TCAGATGGGC TGTGCACACG GTTGAGCCGC    660
CCCTGCCAGA CCTAA                                                      675
```

( 2 ) INFORMATION FOR SEQ ID NO:4:

( i ) SEQUENCE CHARACTERISTICS:
        ( A ) LENGTH: 378 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:4:

```
Met Gly Val Gln Val Glu Thr Ile Ser Pro Gly Asp Gly Arg Thr Phe
 1               5                  10                  15
Pro Lys Arg Gly Gln Thr Cys Val Val His Tyr Thr Gly Met Leu Glu
            20                  25                  30
Asp Gly Lys Lys Phe Asp Ser Ser Arg Asp Arg Asn Lys Pro Phe Lys
        35                  40                  45
Phe Met Leu Gly Lys Gln Glu Val Ile Arg Gly Trp Glu Glu Gly Val
    50                  55                  60
Ala Gln Met Ser Val Gly Gln Arg Ala Lys Leu Thr Ile Ser Pro Asp
65                  70                  75                  80
Tyr Ala Tyr Gly Ala Thr Gly His Pro Gly Ile Ile Pro Pro His Ala
                85                  90                  95
Thr Leu Val Phe Asp Val Glu Leu Leu Lys Leu Glu Gly Leu Val Pro
            100                 105                 110
Arg Gly Ser Met Pro Asp Pro Ala Ala His Leu Pro Phe Phe Tyr Gly
        115                 120                 125
Ser Ile Ser Arg Ala Glu Ala Glu Glu His Leu Lys Leu Ala Gly Met
    130                 135                 140
Ala Asp Gly Leu Phe Leu Leu Arg Gln Cys Leu Arg Ser Leu Gly Gly
145                 150                 155                 160
Tyr Val Leu Ser Leu Val His Asp Val Arg Phe His His Phe Pro Ile
                165                 170                 175
Glu Arg Gln Leu Asn Gly Thr Tyr Ala Ile Ala Gly Gly Lys Ala His
            180                 185                 190
Cys Gly Pro Ala Glu Leu Cys Glu Phe Tyr Ser Arg Asp Pro Asp Gly
        195                 200                 205
Leu Pro Cys Asn Leu Arg Lys Pro Cys Asn Arg Pro Ser Gly Leu Glu
    210                 215                 220
Pro Gln Pro Gly Val Phe Asp Cys Leu Arg Asp Ala Met Val Arg Asp
225                 230                 235                 240
Tyr Val Arg Gln Thr Trp Lys Leu Glu Gly Glu Ala Leu Glu Gln Ala
                245                 250                 255
Ile Ile Ser Gln Ala Pro Gln Val Glu Lys Leu Ile Ala Thr Thr Ala
            260                 265                 270
```

|  |  |  |  |  |  |  |  |  |  |  |  |  |  |  |
|---|---|---|---|---|---|---|---|---|---|---|---|---|---|---|
| His | Glu | Arg<br>275 | Met | Pro | Trp | Tyr | His<br>280 | Ser | Ser | Leu | Thr<br>285 | Arg | Glu | Ala |
| Glu | Arg<br>290 | Lys | Leu | Tyr | Ser<br>295 | Gly | Ala | Gln | Thr | Asp<br>300 | Gly | Lys | Phe | Leu | Leu |
| Arg<br>305 | Pro | Arg | Lys | Glu<br>310 | Gln | Gly | Thr | Tyr | Ala<br>315 | Leu | Ser | Leu | Ile | Tyr | Gly<br>320 |
| Lys | Thr | Val | Tyr | His<br>325 | Tyr | Leu | Ile | Ser | Gln<br>330 | Asp | Lys | Ala | Gly | Lys<br>335 | Tyr |
| Cys | Ile | Pro | Glu<br>340 | Gly | Thr | Lys | Phe | Asp<br>345 | Thr | Leu | Trp | Gln | Leu<br>350 | Val | Glu |
| Tyr | Leu | Lys<br>355 | Leu | Lys | Ala | Asp | Gly<br>360 | Leu | Ile | Tyr | Cys | Leu<br>365 | Lys | Glu | Ala |
| Cys | Pro<br>370 | Asn | Ser | Ser | Ala | Ser<br>375 | Asn | Ala | Ser |

( 2 ) INFORMATION FOR SEQ ID NO:5:

( i ) SEQUENCE CHARACTERISTICS:
        ( A ) LENGTH: 384 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:5:

|  |  |  |  |  |  |  |  |  |  |  |  |  |  |  |
|---|---|---|---|---|---|---|---|---|---|---|---|---|---|---|
| Met<br>1 | Gly | Val | Gln | Val<br>5 | Glu | Thr | Ile | Ser | Pro<br>10 | Gly | Asp | Gly | Arg | Thr<br>15 | Phe |
| Pro | Lys | Arg | Gly<br>20 | Gln | Thr | Cys | Val | Val<br>25 | His | Tyr | Thr | Gly | Met<br>30 | Leu | Glu |
| Asp | Gly | Lys<br>35 | Lys | Phe | Asp | Ser | Ser<br>40 | Arg | Asp | Arg | Asn | Lys<br>45 | Pro | Phe | Lys |
| Phe | Met<br>50 | Leu | Gly | Lys | Gln | Glu<br>55 | Val | Ile | Arg | Gly | Trp<br>60 | Glu | Glu | Gly | Val |
| Ala<br>65 | Gln | Met | Ser | Val | Gly<br>70 | Gln | Arg | Ala | Lys | Leu<br>75 | Thr | Ile | Ser | Pro | Asp<br>80 |
| Tyr | Ala | Tyr | Gly | Ala<br>85 | Thr | Gly | His | Pro | Gly<br>90 | Ile | Ile | Pro | Pro | His<br>95 | Ala |
| Thr | Leu | Val | Phe | Asp<br>100 | Val | Glu | Leu | Leu | Lys<br>105 | Leu | Glu | Gly | Leu | Val<br>110 | Pro |
| Arg | Gly | Ser | Met<br>115 | Ala | Ser | Ser | Gly<br>120 | Met | Ala | Asp | Ser | Ala<br>125 | Asn | His | Leu |
| Pro | Phe<br>130 | Phe | Phe | Gly | Asn | Ile<br>135 | Thr | Arg | Glu | Glu | Ala<br>140 | Glu | Asp | Tyr | Leu |
| Val<br>145 | Gln | Gly | Gly | Met | Ser<br>150 | Asp | Gly | Leu | Tyr | Leu<br>155 | Leu | Arg | Gln | Ser | Arg<br>160 |
| Asn | Tyr | Leu | Gly | Gly<br>165 | Phe | Ala | Leu | Ser | Val<br>170 | Ala | His | Gly | Arg | Lys<br>175 | Ala |
| His | His | Tyr | Thr<br>180 | Ile | Glu | Arg | Glu | Leu<br>185 | Asn | Gly | Thr | Tyr | Ala<br>190 | Ile | Ala |
| Gly | Gly | Arg<br>195 | Thr | His | Ala | Ser | Pro<br>200 | Ala | Asp | Leu | Cys | His<br>205 | Tyr | His | Ser |
| Gln | Glu<br>210 | Ser | Asp | Gly | Leu | Val<br>215 | Cys | Leu | Leu | Lys | Lys<br>220 | Pro | Phe | Asn | Arg |
| Pro<br>225 | Gln | Gly | Val | Gln | Pro<br>230 | Lys | Thr | Gly | Pro | Phe<br>235 | Glu | Asp | Leu | Lys | Glu<br>240 |
| Asn | Leu | Ile | Arg | Glu | Tyr | Val | Lys | Gln | Thr | Trp | Asn | Leu | Gln | Gly | Gln |

```
                         245                            250                            255
Ala  Leu  Glu  Gln  Ala  Ile  Ile  Ser  Gln  Lys  Pro  Gln  Leu  Glu  Lys  Leu
                    260                       265                       270

Ile  Ala  Thr  Thr  Ala  His  Glu  Lys  Met  Pro  Trp  Phe  His  Gly  Lys  Ile
                    275                       280                       285

Ser  Arg  Glu  Glu  Ser  Glu  Gln  Ile  Val  Leu  Ile  Gly  Ser  Lys  Thr  Asn
          290                       295                       300

Gly  Lys  Phe  Leu  Ile  Arg  Ala  Arg  Asp  Asn  Asn  Gly  Ser  Tyr  Ala  Leu
305                           310                      315                      320

Cys  Leu  Leu  His  Glu  Gly  Lys  Val  Leu  His  Tyr  Arg  Ile  Asp  Lys  Asp
                    325                       330                       335

Lys  Thr  Gly  Lys  Leu  Ser  Ile  Pro  Glu  Gly  Lys  Lys  Phe  Asp  Thr  Leu
                    340                       345                       350

Trp  Gln  Leu  Val  Glu  His  Tyr  Ser  Tyr  Lys  Ala  Asp  Gly  Leu  Leu  Arg
               355                       360                       365

Val  Leu  Thr  Val  Pro  Cys  Gln  Lys  Ile  Gly  Thr  Gln  Gly  Asn  Val  Asn
     370                       375                       380
```

( 2 ) INFORMATION FOR SEQ ID NO:6:

( i ) SEQUENCE CHARACTERISTICS:
        ( A ) LENGTH: 224 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:6:

```
Met  Gly  Val  Gln  Val  Glu  Thr  Ile  Ser  Pro  Gly  Asp  Gly  Arg  Thr  Phe
1                   5                        10                       15

Pro  Lys  Arg  Gly  Gln  Thr  Cys  Val  Val  His  Tyr  Thr  Gly  Met  Leu  Glu
               20                       25                       30

Asp  Gly  Lys  Lys  Phe  Asp  Ser  Ser  Arg  Asp  Arg  Asn  Lys  Pro  Phe  Lys
          35                       40                       45

Phe  Met  Leu  Gly  Lys  Gln  Glu  Val  Ile  Arg  Gly  Trp  Glu  Glu  Gly  Val
     50                       55                       60

Ala  Gln  Met  Ser  Val  Gly  Gln  Arg  Ala  Lys  Leu  Thr  Ile  Ser  Pro  Asp
65                       70                       75                       80

Tyr  Ala  Tyr  Gly  Ala  Thr  Gly  His  Pro  Gly  Ile  Ile  Pro  Pro  His  Ala
                    85                       90                       95

Thr  Leu  Val  Phe  Asp  Val  Glu  Leu  Leu  Lys  Leu  Glu  Gly  Leu  Val  Pro
                    100                      105                      110

Arg  Gly  Ser  Met  Ala  Asn  Ser  Leu  Glu  Pro  Glu  Pro  Trp  Phe  Phe  Lys
               115                      120                      125

Asn  Leu  Ser  Arg  Lys  Asp  Ala  Glu  Arg  Gln  Leu  Leu  Ala  Pro  Gly  Asn
     130                      135                      140

Thr  His  Gly  Ser  Phe  Leu  Ile  Arg  Glu  Ser  Glu  Ser  Thr  Ala  Gly  Ser
145                           150                      155                      160

Phe  Ser  Leu  Ser  Val  Arg  Asp  Phe  Asp  Gln  Asn  Gln  Gly  Glu  Val  Val
                    165                      170                      175

Lys  His  Tyr  Lys  Ile  Arg  Asn  Leu  Asp  Asn  Gly  Gly  Phe  Tyr  Ile  Ser
               180                      185                      190

Pro  Arg  Ile  Thr  Phe  Pro  Gly  Leu  His  Glu  Leu  Val  Arg  His  Tyr  Thr
          195                      200                      205

Asn  Ala  Ser  Asp  Gly  Leu  Cys  Thr  Arg  Leu  Ser  Arg  Pro  Cys  Gln  Thr
     210                      215                      220
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: protein     ( x i ) SEQUENCE DESCRIPTION: SEQ ID NO:7:

```
Gly Leu Val Pro Arg Gly Ser
 1               5
```

( 2 ) INFORMATION FOR SEQ ID NO:8:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:8:

```
GATCGCCATG GGAGTGCAGG TGGAAACCAT CTCCCCA                    37
```

( 2 ) INFORMATION FOR SEQ ID NO:9:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:9:

```
TACGAATTCT GGCGTGGATC CACGCGGAAC CAGACCTTCC AGTTTTAG         48
```

( 2 ) INFORMATION FOR SEQ ID NO:10:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:10:

```
ATTAGGATCC ATGCCAGATC CTGCAGCTCA CCTGCCCT                    38
```

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear     ( i i ) MOLECULE TYPE: Genomic DNA     ( x i ) SEQUENCE DESCRIPTION: SEQ ID NO:11:

```
ATATGGATCC TTACCAGAGG CGTTGCT                               27
```

( 2 ) INFORMATION FOR SEQ ID NO:12:

( i ) SEQUENCE CHARACTERISTICS:
  ( A ) LENGTH: 34 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO:12:

CAATAGGATC CATGGCCAGC AGCGGCATGG CTGA    34

( 2 ) INFORMATION FOR SEQ ID NO:13:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO:13:

GACCTAGGAT CCCTAATTAA CATTTCCCTG TGTGCCGAT    39

( 2 ) INFORMATION FOR SEQ ID NO:14:

( i ) SEQUENCE CHARACTERISTICS:
  ( A ) LENGTH: 38 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO:14:

ATATGGATCC ATGGCGAACA GCCTGGAGCC CGAACCCT    38

( 2 ) INFORMATION FOR SEQ ID NO:15:

( i ) SEQUENCE CHARACTERISTICS:
  ( A ) LENGTH: 43 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO:15:

ATTAGGATCC TTAGGTCTGG CAGGGGCGGC TCAACCGTGT GCA    43

( 2 ) INFORMATION FOR SEQ ID NO:16:

( i ) SEQUENCE CHARACTERISTICS:
  ( A ) LENGTH: 22 amino acids
  ( B ) TYPE: amino acid
  ( C ) STRANDEDNESS: single
  ( D ) TOPOLOGY: linear ( i i ) MOLECULE TYPE: protein ( i x ) FEATURE:
  ( A ) NAME/KEY: Other
  ( B ) LOCATION: 6...6
  ( D ) OTHER INFORMATION: Xaa =Phosphorylated Tyrosine
  ( A ) NAME/KEY: Other
  ( B ) LOCATION: 17...17
  ( D ) OTHER INFORMATION: Xaa =Phosphorylated Tyrosine ( x i ) SEQUENCE DESCRIPTION: SEQ ID NO:16:

Gly Ser Asn Gln Leu Xaa Asn Glu Leu Asn Leu Gly Arg Arg Glu Glu
 1           5                  10                  15

```
Xaa  Asp  Val  Leu  Asp  Lys
                20
```

( 2 ) INFORMATION FOR SEQ ID NO:17:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear     ( i i ) MOLECULE TYPE: protein     ( i x ) FEATURE:
        ( A ) NAME/KEY: Other
        ( B ) LOCATION: 4...4
        ( D ) OTHER INFORMATION: Xaa =Phosphorylated Tyrosine     ( x i ) SEQUENCE DESCRIPTION: SEQ ID NO:17:

```
Glu  Pro  Gln  Xaa  Glu  Glu  Ile  Pro  Ile  Tyr  Leu
 1              5                         10
```